(12) United States Patent
Rossen et al.

(10) Patent No.: US 12,053,248 B2
(45) Date of Patent: Aug. 6, 2024

(54) ULTRASOUND-GUIDED TRANSPERINEAL AND/OR TRANSRECTAL BIOPSY

(71) Applicant: B-K Medical Aps, Herlev (DK)

(72) Inventors: Rasmus Holdensgaard Rossen, Vanlose (DK); Torben Svanberg Nielsen, Kobenhav S (DK); Mai Hestbek, Copenhagen (DK); Fredrik Gran, Limhamn (SE); Henrik Jensen, Nordhavn (DK)

(73) Assignee: B-K MEDICAL APS, Herlev (DK)

( * ) Notice: Subject to any disclaimer, the term of this patent is extended or adjusted under 35 U.S.C. 154(b) by 0 days.

(21) Appl. No.: 17/593,088

(22) PCT Filed: Mar. 12, 2019

(86) PCT No.: PCT/IB2019/051998
§ 371 (c)(1),
(2) Date: Sep. 9, 2021

(87) PCT Pub. No.: WO2020/183226
PCT Pub. Date: Sep. 17, 2020

(65) Prior Publication Data
US 2022/0273373 A1    Sep. 1, 2022

(51) Int. Cl.
*A61B 34/20* (2016.01)
*A61B 8/00* (2006.01)
(Continued)

(52) U.S. Cl.
CPC ............ *A61B 34/20* (2016.02); *A61B 8/0841* (2013.01); *A61B 8/12* (2013.01); *A61B 8/445* (2013.01);
(Continued)

(58) Field of Classification Search
CPC . A61B 8/0841; A61B 2017/3413; A61B 8/12; A61B 34/20; A61B 90/11; A61B 90/10
See application file for complete search history.

(56) References Cited

U.S. PATENT DOCUMENTS 4,911,173 A * 3/1990 Terwilliger ........ A61B 17/3403
                                                    600/101
2007/0255168 A1* 11/2007 Hibner ............... A61B 10/0266
                                                    600/562
(Continued)

OTHER PUBLICATIONS

International Search Report for PCT/IB2019/051998 published as WO2020183226 on Sep. 17, 2020.
(Continued)

*Primary Examiner* — Colin T. Sakamoto
*Assistant Examiner* — Tommy T Ly
(74) *Attorney, Agent, or Firm* — Daugherty & Del Zoppo, Co. LPA

(57) ABSTRACT

A system (502) includes an elongate ultrasound imaging probe (504) with a long axis and a top side that extends along the long axis. The elongate ultrasound imaging probe includes an elongate tubular handle (606; 1606), a head (1608), an elongate tubular shaft (608; 1610) between the elongate tubular handle and the head, and a transducer array (514) disposed in the head and configured to transmit in a sagittal plane, which is a plane that cuts through the long axis of the elongate tubular shaft, only in a direction extending out from the top side. The elongate tubular handle is both not centered on the elongate tubular shaft and not shifted down in the sagittal plane away from the top.

14 Claims, 7 Drawing Sheets

(51) Int. Cl.
*A61B 8/08* (2006.01)
*A61B 8/12* (2006.01)
*A61B 10/02* (2006.01)

(52) U.S. Cl.
CPC ............ *A61B 8/4488* (2013.01); *A61B 8/463* (2013.01); *A61B 10/0233* (2013.01); *A61B 2034/2051* (2016.02); *A61B 2034/2055* (2016.02); *A61B 2034/2059* (2016.02); *A61B 2034/2063* (2016.02)

(56) References Cited

U.S. PATENT DOCUMENTS

| | | | |
|---|---|---|---|
| 2010/0022871 A1* | 1/2010 | De Beni | A61B 8/0833 600/443 |
| 2011/0009748 A1 | 1/2011 | Green et al. | |
| 2015/0065886 A1 | 3/2015 | Stoianovici et al. | |
| 2015/0282880 A1 | 10/2015 | Allaway | |
| 2016/0022309 A1 | 1/2016 | Allaway | |
| 2018/0325602 A1* | 11/2018 | Bharat | A61B 34/10 |
| 2019/0175214 A1* | 6/2019 | Wood | A61B 17/3403 |
| 2020/0054357 A1* | 2/2020 | Ihatsu | A61B 8/0841 |

OTHER PUBLICATIONS

Ultrasound Medical Corporation, SonixGPS Specifications Sheet Precision Ultrasound Guidance for Biopsies and Line Placement, 4 sheets, 00.050.089 Rev. A, entire document.

\* cited by examiner

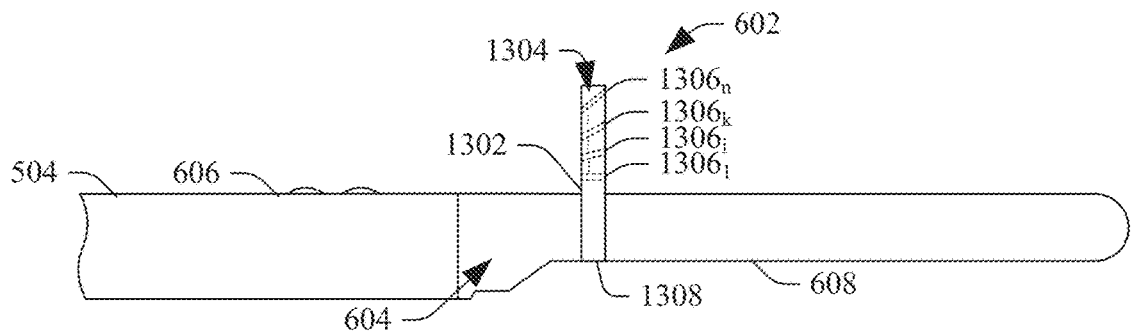
FIGURE 13
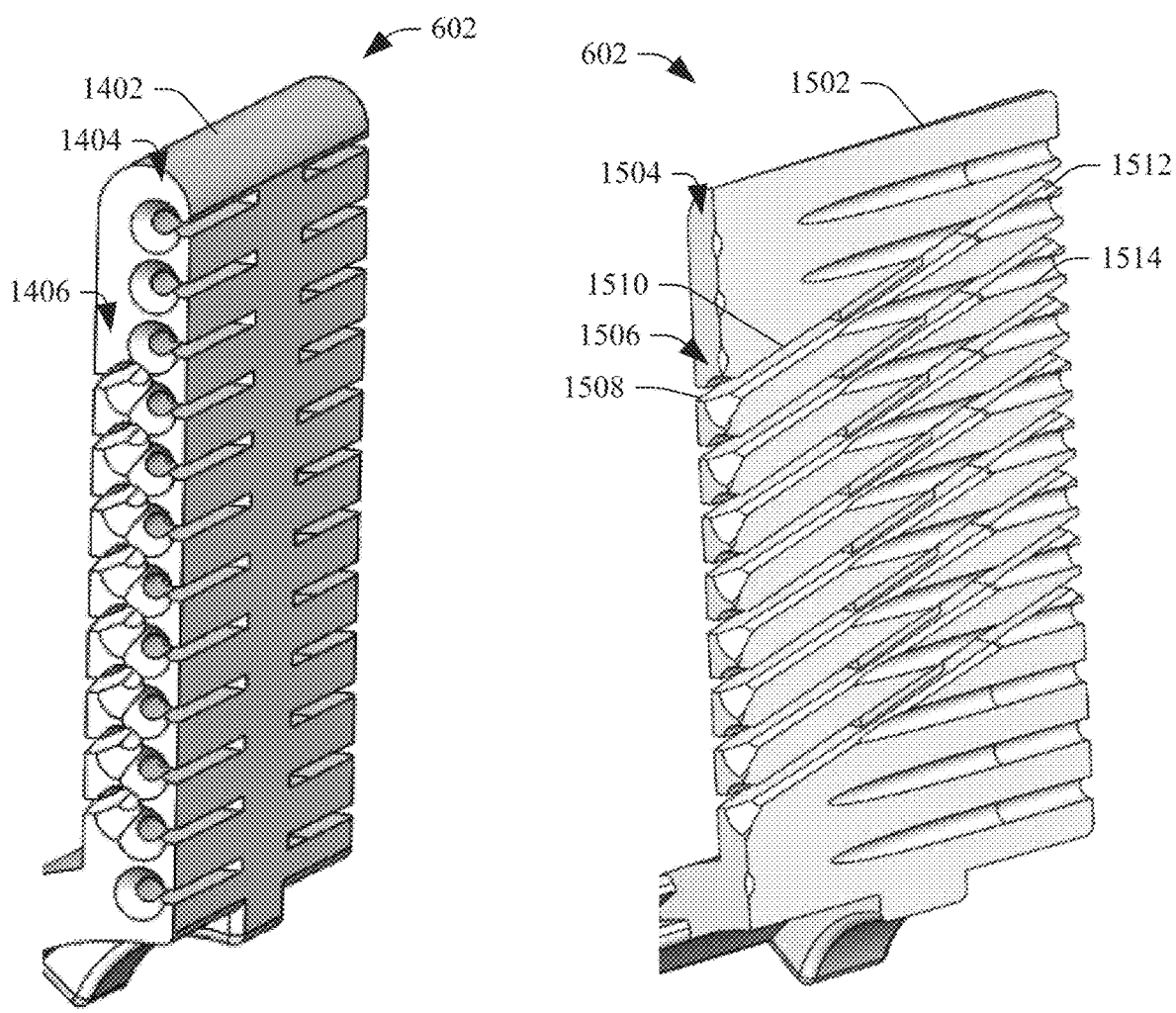
FIGURE 14
FIGURE 15

ULTRASOUND-GUIDED TRANSPERINEAL AND/OR TRANSRECTAL BIOPSY

RELATED APPLICATION

This application is a national filing of PCT application Serial No. PCT/IB2019/051998, filed Mar. 12, 2019, published as WO2020/183226 on Sep. 17, 2020.

TECHNICAL FIELD

The following generally relates to ultrasound imaging and more particularly to ultrasound-guided transperineal and/or transrectal biopsy.

BACKGROUND

Ultrasound imaging has provided useful information about the interior characteristics of an object or subject under examination. One application includes ultrasound-guided (transrectal or transperineal) prostate biopsy. Generally, a prostate biopsy is a procedure to remove a tissue sample(s) from a suspect area of the prostate, e.g., to rule out/diagnose cancer.

With a transrectal prostrate biopsy procedure, the ultrasound imaging probe and the biopsy instrument are inserted into the rectum via the anus and the biopsy instrument is used to acquire a sample(s) from the prostrate through the rectal wall. With a transperineal prostate biopsy procedure, the ultrasound imaging probe is inserted into the rectum via the anus and the biopsy instrument is used to acquire a sample(s) from the prostate through the perineum, which is the region behind the scrotum and in front of the anus. In both instance, ultrasound imaging is used to guide the biopsy instrument to the target area of the prostate. A trend has been to perform transperineal biopsies, e.g., because of the risk of infection due to puncturing the rectal wall along with antibiotic resistant bacteria with transrectal biopsies.

Transperineal biopsies have been performed with either a parallel trajectory or a fan/angled trajectory, using either a physical guide or free-hand. FIG. 1 shows an example diagram of a side view of a portion of an ultrasound probe 102 in connection with a sagittal plane of a prostate 104 along with a parallel biopsy needle trajectory 106. As shown, unfortunately, the parallel biopsy needle trajectory 106 can experience physical interference from a pubic archbone 108, limiting access to an apex 110 of an anterior region 112 of the prostate 104. An angled biopsy needle trajectory may be able to reach the apex 110, however, the biopsy instrument may puncture the rectal wall when sampling a peripheral region 114, e.g., because of the combination of the extent of the biopsy instrument and poor visualization of the needle in the ultrasound image.

FIGS. 2 and 3 show examples of free-hand transrectal biopsies. Both figures show a top-down view of a probe 202, which includes a head 204, a shaft 206, a handle 208, and a cut-out 210 in the shaft 206 to provide space for a needle 212 to be advanced along a center line 214 of the probe 202. In FIG. 2, the needle 212 is advanced from above the probe 202 and along a top side 216 of the shaft 206. In FIG. 3, the needle 212 is advanced from below the probe 202 up through the cut-out 210 and along the top side 216 of the shaft 206. Unfortunately, these approaches are inflexible in that the range of possible trajectories is limited at least because a portion 216 of the handle 208 is physically in the way and prevents certain trajectories. FIG. 4 shows a side view of the probe 202 of FIGS. 2 and 3, where the portion 216 prevents trajectories between a trajectory 402 (for FIG. 2) and a trajectory 404 (for FIG. 3).

Transperineal biopsies performed with a guide have used a stationary guide that is in firm contact with the probe so that a needle path can be determined a priori and superimposed on an ultrasound image and displayed for tracking and guidance. US 2015/0282880 A1 and US 2016/0022309 A1 discuss setups where the needle is in firm contact with the probe, and US 2011/0009748 A1 discusses a transperineal biopsy that utilizes a guide with predetermined holes for only parallel trajectories. Unfortunately, these approaches constrain how the biopsy is acquired. That is, the biopsy trajectories are constrained to the parallel paths determined by the predetermined guide holes and shown on the displayed image of the predetermined needle paths.

SUMMARY

Aspects of the application address the above matters, and others.

In one aspect, a system includes an elongate ultrasound imaging probe with a long axis and a top side that extends along the long axis. The elongate ultrasound imaging probe includes an elongate tubular handle, a head, an elongate tubular shaft between the elongate tubular handle and the head, and a transducer array disposed in the head and configured to transmit in a sagittal plane, which is a plane that cuts through the long axis of the elongate tubular shaft, only in a direction extending out from the top side. The elongate tubular handle is both not centered on the elongate tubular shaft and not shifted down in the sagittal plane away from the top.

In another aspect, a system includes a needle biopsy guide. The needle biopsy guide includes a first portion configured to couple to the elongate ultrasound imaging probe, and a hollow channel configured to guide a needle or a canula along a trajectory that is parallel to the long axis and along a trajectory that is angled to the long axis.

In yet another aspect, a system includes an elongate ultrasound imaging probe including a first tracking device, a needle biopsy instrument including a second tracking device, a tracking system configured to track a spatial location of the needle biopsy instrument and the elongate ultrasound imaging probe based on signals from the first and second tracking devices, an image processor configured select a plane from volumetric image data generated with ultrasound echoes detected by a transducer array of the elongate ultrasound imaging probe based on the tracked spatial locations, wherein the plane includes an entry point of the needle biopsy instrument in an object and at least a trajectory of the needle biopsy instrument in the object, and a display configured to display the selected plane.

Those skilled in the art will recognize still other aspects of the present application upon reading and understanding the attached description.

BRIEF DESCRIPTION OF THE DRAWINGS

The application is illustrated by way of example and not limited by the figures of the accompanying drawings, in which like references indicate similar elements and in which:

FIG. 13 diagrammatically illustrates a side view of another example biopsy needle guide that includes a block with predetermined parallel and angled biopsy trajectory channels in accordance with an embodiment(s) herein;

FIG. 14 diagrammatically illustrates a perspective view of yet another example biopsy needle guide that includes a column of parallel biopsy trajectory paths and a column of angled biopsy trajectory paths in accordance with an embodiment(s) herein;

FIG. 15 diagrammatically illustrates a perspective view of still another example biopsy needle guide that includes a single column of biopsy trajectory paths wherein each path includes a parallel branch and an angled branch in accordance with an embodiment(s) herein;

DETAILED DESCRIPTION

Figure 5:
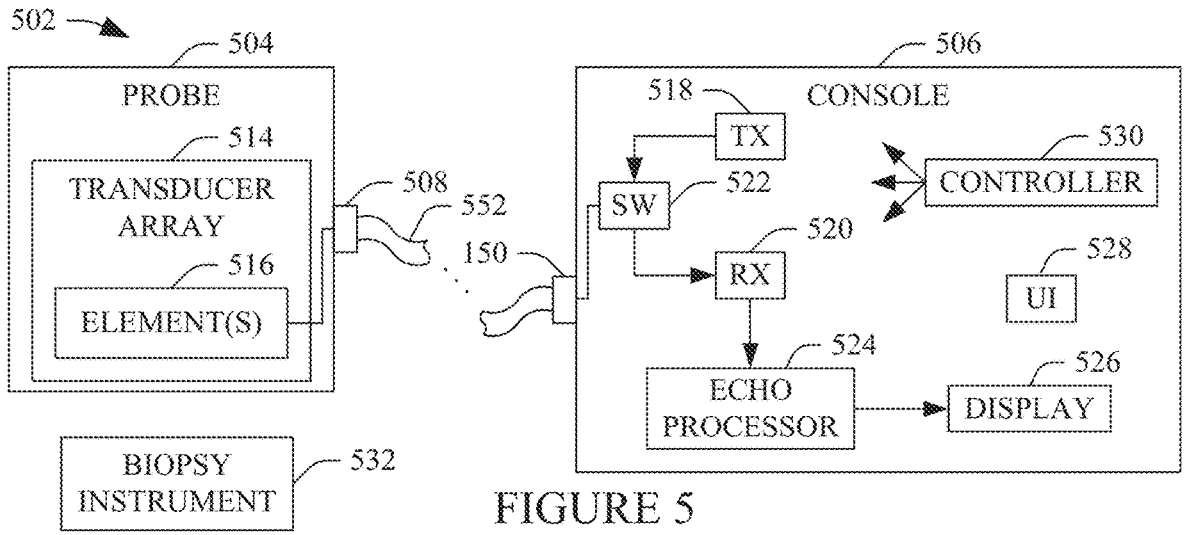
FIG. 5 diagrammatically illustrates an example ultrasound system in connection with a biopsy instrument in accordance with an embodiment(s) herein.

FIG. 5 illustrates an example imaging system 502 such as an ultrasound imaging system/scanner. The imaging system 502 includes a probe 504 and a console 506, which interface with each other through suitable complementary hardware (e.g., cable connectors 508 and 510 and a cable 512 as shown, etc.) and/or wireless interfaces (not visible).

The probe 504 includes a transducer array 514 with one or more transducer elements 516. The one or more transducer elements 516 are arranged as a 1-D or 2-D, linear, curved and/or otherwise shaped, fully populated or sparse, etc. array. The elements 516 are configured to convert excitation electrical pulses into an ultrasound pressure field and convert a received ultrasound pressure field (an echo) into electrical (e.g., a radio frequency (RF)) signals.

The console 506 includes transmit circuitry (TX) 518 configured to generate the excitation electrical pulses and receive circuitry (RX) 520 configured to process the RF signals, e.g., amplify, digitize, and/or otherwise process the RF signals. The console 506 further includes a switch (SW) 522 configured to switch between the TX 518 and RX 520 for transmit and receive operations, e.g., by electrically connecting and electrically disconnecting the TX 518 and the RX 520.

The console 506 includes further an echo processor 524 configured to process the signal from the RX 520. For example, in one instance the echo processor 524 is configured to beamform (e.g., delay-and-sum) the signal to construct a scanplane of scanlines of data. The echo processor 524 can process data from 1-D and/or 2-D probes for 2-D, 3-D and/or 4-D applications. The echo processor 524 can be implemented by a hardware processor such as a central processing unit (CPU), a graphics processing unit (GPU), a microprocessor, etc.

The console 506 further includes a display 526. The output of the echo processor 524 is scan converted to the coordinate system of the display 526 and displayed as images via the display 526. In one instance, the scan converting includes changing the vertical and/or horizontal scan frequency of signal based on the display 526. The scan converter 128 can be configured to employ analog scan converting techniques and/or digital scan converting techniques.

The console 506 further includes a user interface 528, which includes one or more input devices (e.g., a button, a touch pad, a touch screen, etc.) and one or more output devices (e.g., a display screen, a speaker, etc.). The console 506 further includes a controller 530 configured to control one or more of the probe 504, the transmit circuitry 518, the receive circuitry 520, the switch 522, the echo processor 524, the display 526, the user interface 528, and/or one or more other components of the imaging system 502.

In the illustrated embodiment, the imaging system 502 is used in connection with a biopsy instrument 532. In this embodiment, the imaging system 502 is used to guide a needle of the biopsy instrument 532 to a target region within an object or subject where the biopsy instrument 532 is used to acquire a sample of the target region.

As described in greater detail below, a biopsy guide that provides for both parallel and angled trajectories can be employed with the probe 504 for prostrate biopsies. In one instance, this allows for taking biopsies more precisely at the peripheral zone while also being able to avoid the pubic archbone that can block access to the anterior apex. Also described in greater detail below, a handle of the probe 504 can be translated sideways so that it does not interfere with the sagittal plane. In one instance, this allows a needle trajectory path that was not previously possible. Also described in greater detail below, a tracking system can be employed with the imaging system 502. In one instance, this provides the flexibility of freehand biopsies with the accuracy of ultrasound-guided biopsies, making transperineal biopsies more versatile.

Figure 6:
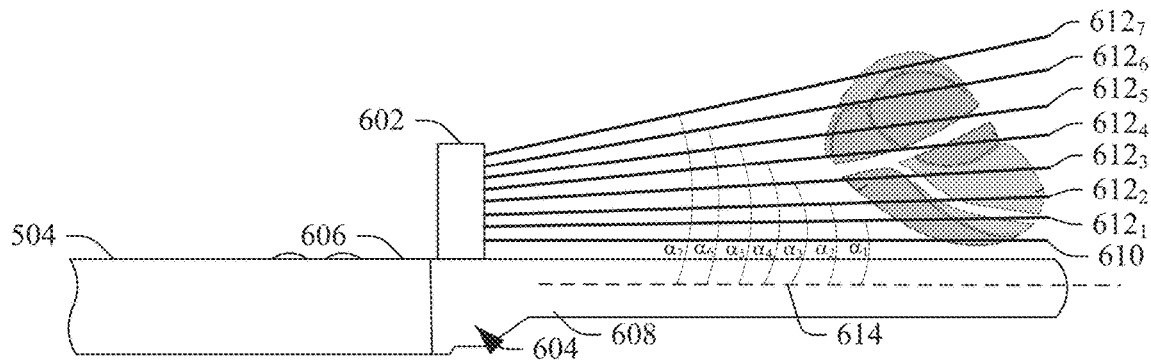
FIG. 6 diagrammatically illustrates a side view of an example biopsy needle guide configured with both parallel and angled trajectory paths coupled to a probe in accordance with an embodiment(s) herein.
Figure 7:
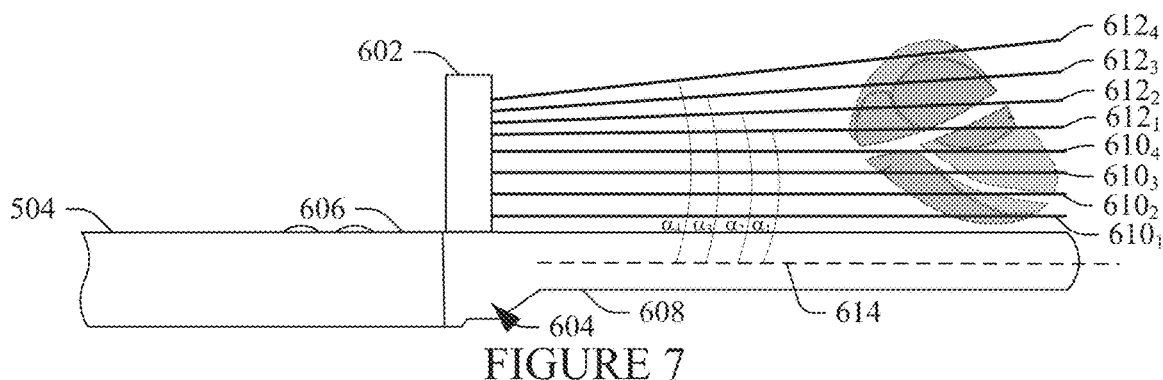
FIG. 7 diagrammatically illustrates a side view of another example biopsy needle guide configured with both parallel and angled trajectory paths coupled to a probe in accordance with an embodiment(s) herein.

FIGS. 6 and 7 illustrate a non-limiting example of the probe 504 in connection with a guide 602 such as a biopsy needle guide. In this example, the guide 602 is supported at a region 604 between an elongate tubular handle 606 and an elongate tubular shaft 608 of the probe 504. In other embodiments, the guide 602 is supported on the handle 606, on the shaft 608, or a combination of the handle 606, the region 604 and/or the shaft 608. The guide 602, in one instance, is supported via a clamping and/or other device. In these examples, the guide 602 is a physical device preconfigured with a plurality of channels (not visible).

In FIG. 6, the plurality of channels includes a single channel that provides a trajectory 610 that is parallel to an axis 614 of the shaft 608 and multiple channels that provide trajectories $612_1$, $612_2$, $612_3$, $612_4$, $612_5$, $612_6$, and $612_7$ that are angled, with increasing angle $\alpha_1$, $\alpha_2$, $\alpha_3$, $\alpha_4$, $\alpha_5$, $\alpha_6$, and $\alpha_7$, to the axis 614 of the shaft 608. In FIG. 7, the plurality of channels includes multiple channels that provide trajectories $610_1$, $610_2$, $610_3$ and $610_4$ that are parallel, with increasing distance, to the axis 614 of the shaft 608 and multiple channels that provide trajectories $612_1$, $612_2$, $612_3$ and $612_4$ that are angled, with increasing angle $\alpha_1$, $\alpha_2$, $\alpha_3$ and $\alpha_4$, to the axis 614 of the shaft 608.

Figure 8:
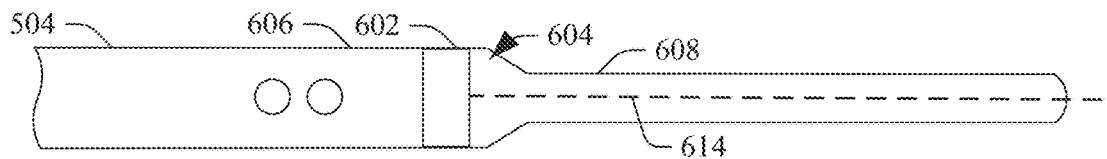
FIG. 8 diagrammatically illustrates a top-down view of the example biopsy needle guides of FIGS. 6 and/or 7 in accordance with an embodiment(s) herein.

In both FIG. 6 and FIG. 7, the guide 602 provides trajectories to the peripheral zone 114 and the apex 110 of the anterior zone 112 of the prostate 104, including a trajectory to the apex 110 that avoids physical inference from the pubic archbone 108. In FIG. 6, the former includes the parallel trajectory 610 and the latter includes the trajectory $612_7$. In FIG. 7, the former includes the parallel trajectory $610_1$ and the latter includes the trajectory $612_4$. FIG. 8 shows a top down view where the guide 602 is centered in the region 604 on the axis 614.

In a variation, the guide 602 includes more, less and/or other channels for other trajectories. This may include interlaced channels for channels parallel and angled trajectories. This may also include angled trajectories that do not all increase with a distance from the axis 614. Furthermore, in another instance, the guide 602 is not centered in the region 604 on the axis 614. Other configurations are also contemplated herein.

Figure 9:
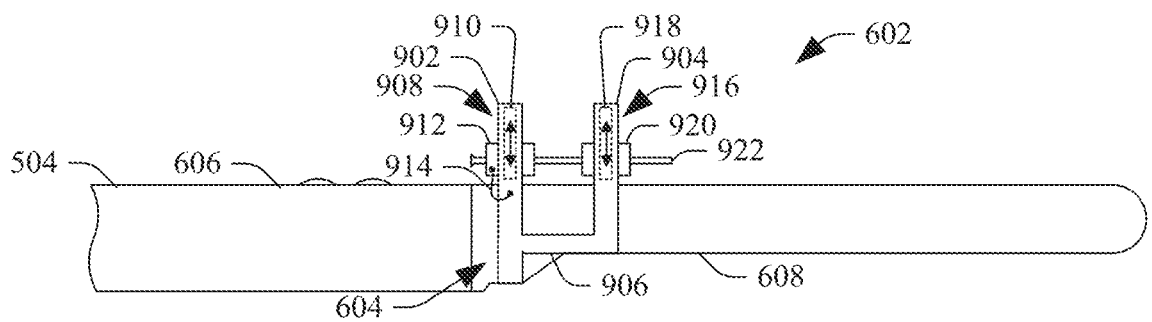
FIG. 9 diagrammatically illustrates a side view of yet another example biopsy needle guide at a first position which provides a parallel trajectory in accordance with an embodiment(s) herein.
Figure 10:
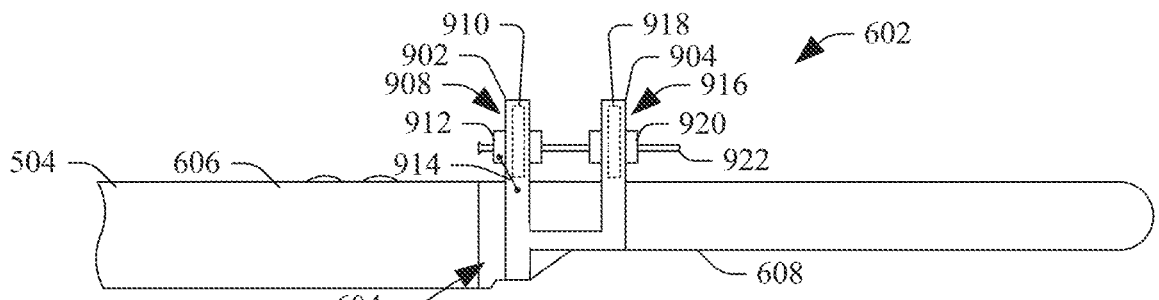
FIG. 10 diagrammatically illustrates the side view with the biopsy needle guide at another position which provides a parallel trajectory in accordance with an embodiment(s) herein.
Figure 11:
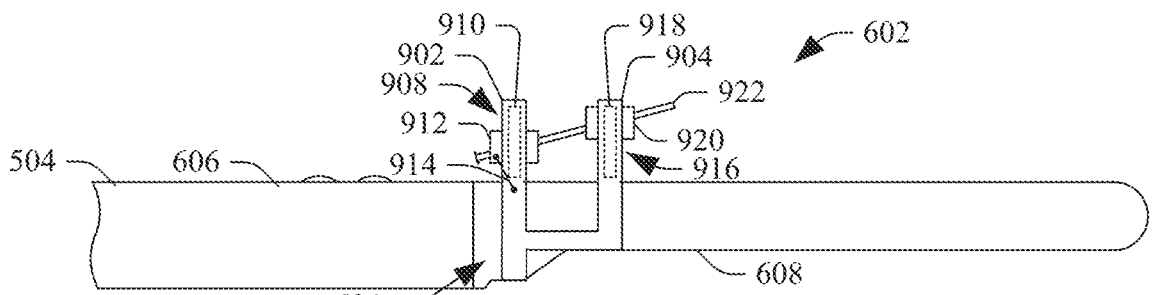
FIG. 11 diagrammatically illustrates the side view with the biopsy needle guide at a position which provides an angled trajectory in accordance with an embodiment(s) herein.

FIGS. 9-11 illustrate a non-limiting example of the guide 602. In this example, the guide 602 includes a vertical leg 902 having a length, a second vertical leg 906 having a length, and a horizontal leg 906. The length of the vertical leg 902 is greater than the length of the vertical leg 904. The vertical leg 902 clamps onto the region 604. The second vertical leg 904 is attached to the first vertical leg 902 through the horizontal leg 906.

The first vertical leg 902 includes an opening 908 in which a stationary part 910 of a linear bearing is disposed. A moveable part 912 of the linear bearing is engaged with the stationary part 910 and configured to move vertically within the first vertical leg 902. In this example, a limiter 914 (e.g., a wire, string, etc.) limits the vertical motion from an initial position in which the moveable part 912 is closest to the shaft 608 to a position at or less than a maximum position furthest away from the shaft 608.

The second vertical leg 904 includes an opening 916 in which a stationary part 918 of a linear bearing is disposed. A moveable part 920 of the linear bearing is engaged with the stationary part 918 and configured to move vertically within the second vertical leg 904. In this example, the moveable part 920 is free to move from the initial position in which the moveable part 920 is closest to the shaft 608 to the maximum position/the position furthest away from the shaft 608.

In this example, the moveable parts 912 and 920 are configured to support a trocar 922, which is configured to allow a biopsy needle to pass therethrough. In general, the trocar 922 is inserted through an incision in the perineum and provides access to the prostate with the biopsy needle without any further punctures through the skin, unless otherwise desired. In FIG. 9, both of the moveable parts 912 and 920 are at their lowest positions and together provide a parallel trajectory (e.g., $610_1$ in FIG. 7) to the prostate.

In FIG. 10, both moveable parts 912 and 920 are moved vertically to a same position at which the limiter 914 limits the moveable part 920 from further vertical motion. In this position, the moveable parts 912 and 920 together provide another parallel trajectory (e.g., $610_4$ in FIG. 7) to the prostate. In FIG. 11, the moveable part 920 is moved vertically to its maximum allowable position. In this position, the moveable parts 912 and 920 together provide an angled trajectory (e.g., $612_4$ in FIG. 7) to the prostate.

In one instance, both moveable parts 912 and 920 move together between the lower limit and the limit of the limiter 914. In another instance, the moveable parts 912 and 920 move independently between the lower limit and the limit of the limiter 914. The moveable parts 912 and 920 can be moved by way of linear translation of a handle, a rotational-to-linear translation of a rotary dial, a pivotal-to-linear translation of a lever, and/or other mechanism. A locking mechanism can be used to hold them in place.

In a variation, both moveable parts 912 and 920 of the bearings are configured to hold the biopsy needle in alternative to or in addition to the trocar 922. In this configuration, the biopsy needle is slidable within the moveable parts 912 and 920 to allow the biopsy needle to be advanced to the prostate to take a sample and retracted from the prostate after a sample is taken. Furthermore, other guide shapes, locations of attachment, and/or moving mechanisms are contemplated herein.

Figure 12:
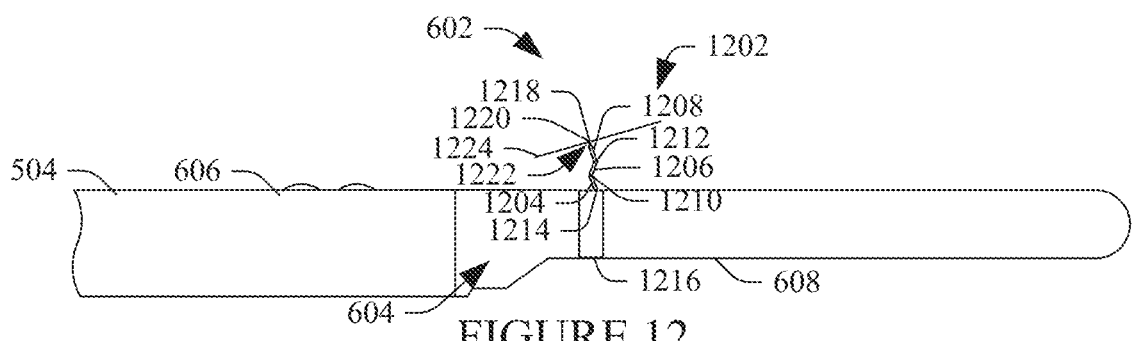
FIG. 12 diagrammatically illustrates a side view of another example biopsy needle guide that includes a mechanical arm in accordance with an embodiment(s) herein.

FIG. 12 illustrate another non-limiting example of the guide 602. In this example, the guide 602 attaches to the shaft 608 and includes a mechanical arm 1202 with multiple segments 1204, 1206 and 1208 which are connected together by joints 1210 and 1212 which are configured to move in one direction along one axis, within a plane defined by two axes, or within a volume defined by three axes.

A first end 1214 of the mechanical arm 1202 is affixed to a clamp 1216 attached to the shaft 608. A second end 1218 at an opposing end of the mechanical arm 1202 includes a member 1220 with a guide hole 1222 configured to allow a biopsy needle 1224 to pass therethrough. In general, this embodiment allows free-hand positioning of biopsy needle 1224 under the guidance of the mechanical arm 1202. In a variation, there are more or less segments and/or joints.

With the configurations of FIGS. 9-12, a biopsy procedure can be performed with a single perforation point in the perineum to obtain multiple samples, e.g., from the peripheral zone 114 to the anterior apex 110, by tilting/pivoting the guide 602. Alternatively, the biopsy procedure can be performed through multiple perforation points in the perineum, each corresponding to a different trajectory to acquire a different sample.

FIG. 13 illustrates yet another non-limiting examples of the guide 602. In FIG. 13 the guide 602 includes a block 1302 with a column 1304 of predetermined channels $1306_1, \ldots, 1306_i, \ldots, 1306_k, \ldots, 1306_n$, where n is a positive integer, and an end 1308 that clamps to the shaft 608. In this example, the channel $1306_1$ provides a parallel trajectory and the channels $1306_i, \ldots, 1306_k, \ldots, 1306_n$ provide angled trajectories.

FIG. 14 illustrates yet another non-limiting examples of the guide 602. In FIG. 14 the guide 602 includes a block 1402 with two columns 1404 and 1406 of predetermined channels. In this example, the column 1404 includes channels that provide parallel biopsy needle trajectories and the column 1406 includes channels that provide angled biopsy needle trajectories.

FIG. 15 illustrates still another non-limiting examples of the guide 602. In FIG. 15 the guide 602 includes a block 1502 with a single column 1504 of predetermined channels. In this example, each channel 1506 includes a single entry point 1508 and a single path 1510 partway through the guide 602 and then alternative branches 1512 and 1514 thereafter, where the branch segment 1512 provides a parallel biopsy needle trajectory, and the branch 1514 provides an angled biopsy needle trajectory.

Figure 23:
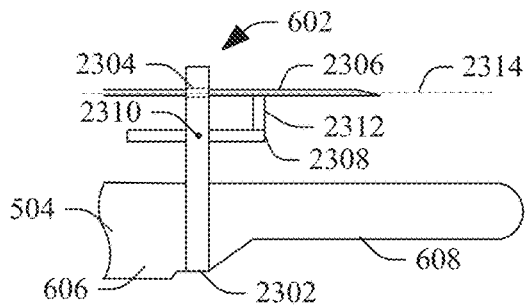
FIG. 23 illustrates yet another example biopsy needle guide at a first position which provides a parallel trajectory in accordance with an embodiment(s) herein.
Figure 24:
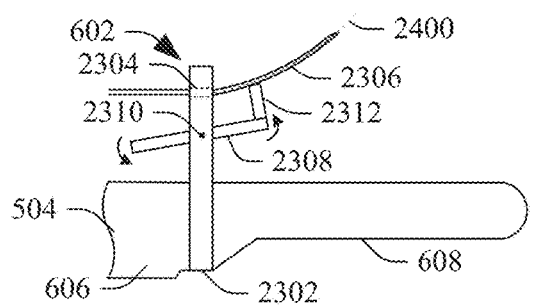
FIG. 24 illustrates the biopsy guide of FIG. 23 in which an actuator physically contacts and bends a needle or canula to provide an angled trajectory in accordance with an embodiment(s) herein.

FIGS. 23 and 24 illustrate yet another non-limiting examples of the guide 602. In this example, the guide 602 includes a support 2302 configured to couple to the probe 504, an access channel 2304 is configured to support a needle instrument 2306 (e.g., a needle or a canula), and an actuator 2308 is pivotably mounted to the support 2302 at a pivot point 2310. In this example, the actuator 2308 is a cuboid shaped with a nub 2312 at an end proximal to the shaft 608. Other shapes are also contemplated herein. In the non-actuating state (FIG. 23), the nub 2312 is just below or just touching the needle instrument 2306 allowing for a parallel trajectory 2314 with respect to the shaft 608.

In an actuating state (FIG. 24), the actuator 2308 is pivoted about the pivot point 2310 in a direction towards the handle 606. As a result, the opposing end pivots about the pivot point 2310 away from the shaft 608, which causes the nub 2408 to physically contact the needle instrument 2406 (if not already in physical contact) and urge the needle instrument 2306 away from the shaft 608, which causes the needle instrument 2306 to bend or elastically deform, creating an angled trajectory 2400. The illustrated trajectory is not limiting, and the actuator 2308 can be pivoted more or less to create other angled trajectories.

Figure 1:
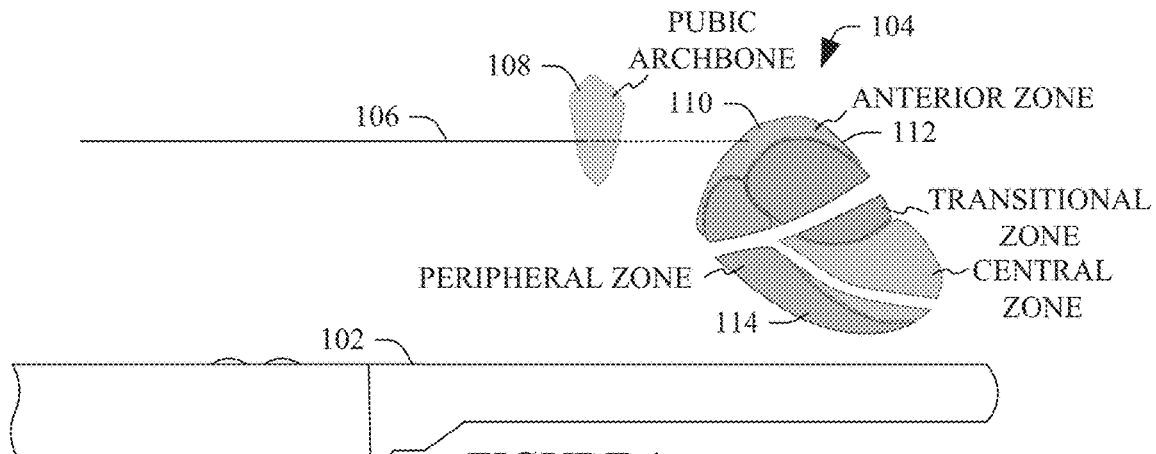
FIG. 1 illustrates a prior art example of a parallel biopsy needle trajectory for a prostrate biopsy procedure.

With the configurations of FIGS. 6-15, 23 and 24, in one instance, biopsies can be taken more precisely at the peripheral zone 114 (FIG. 1), which is where most cancers occur, while also being able to avoid the pubic archbone (FIG. 1) that can block access to the anterior apex 110 (FIG. 1).

Figure 16:
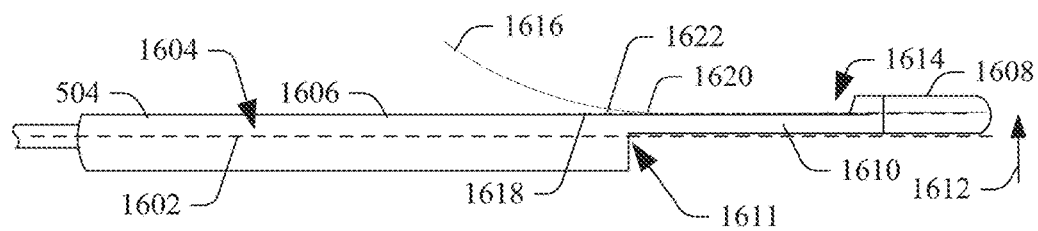
FIG. 16 illustrates a top down view of a probe configured such that its handle does not interfere with biopsy needle trajectories in accordance with an embodiment(s) herein.
Figure 17:
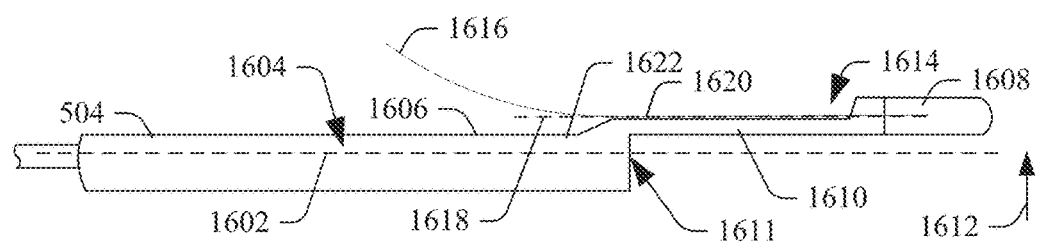
FIG. 17 illustrates a top down view of another probe configured such that its handle does not interfere with biopsy needle trajectories in accordance with an embodiment(s) herein.
Figure 18:
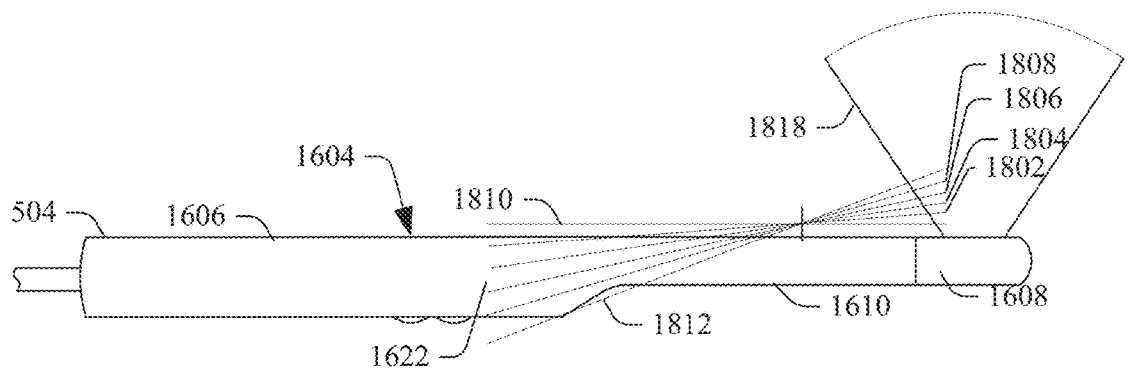
FIG. 18 illustrates a side view of the probe of FIG. 16 or 17 showing several available biopsy needle trajectories in accordance with an embodiment(s) herein.

FIGS. 16-18 illustrate another embodiment of the probe 504. In this example, the probe 504 has a long axis 1602 and a top side 1604 that extends along the long axis 1602. The probe 504 further includes an elongate tubular handle 1606, a head 1608, and an elongate tubular shaft 1610 disposed between the elongate tubular handle 1606 and the head 1608. The transducer array 514 (FIG. 5) is disposed in the head 1608 and is configured to transmit in a sagittal plane (i.e. the plane cutting through a center line 1618 of the shaft 1610) extending in a direction only out from the top side 1604. The elongate tubular shaft 1610 is coupled to the elongate tubular handle 1606 linearly offset from a center 1611 of the elongate tubular handle 1606 in a direction transverse 1612 to the long axis 1602 and the sagittal plane.

FIGS. 16 and 17 illustrate a top-down view of the probe 504. The elongate tubular shaft 1610 includes a recessed region 1614 to provide space for a needle 1616 to be advanced along the center line 1618 of the shaft 1610. In FIG. 16, a surface 1620 of the recessed region 1614 is flush with a surface of a side 1622 of the handle 1606 forming a planar surface therewith. In FIG. 17, the surface 1620 of the recessed region 1614 protrudes out relative to the surface of a side 1622 of the handle 1606. With both FIGS. 16 and 17, the needle 1616 can be advanced from below (or above) the handle 1606 to above (or below) the handle 1606 without any physical interference from the probe 504.

Figure 2:
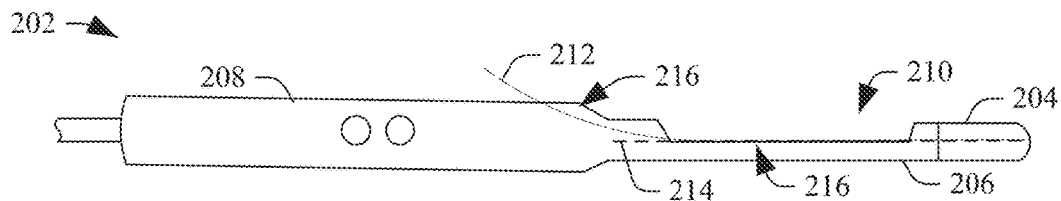
FIG. 2 illustrates a top down view of prior art parallel biopsy needle trajectory advanced from a top of a probe.
Figure 3:
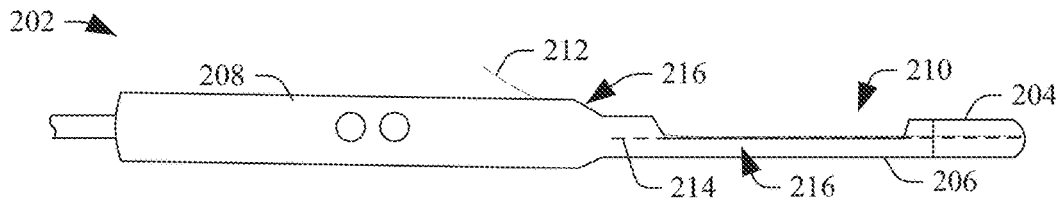
FIG. 3 illustrates a top down view of prior art angled biopsy needle trajectory advanced from a bottom of a probe up to and along the top of the probe.
Figure 4:
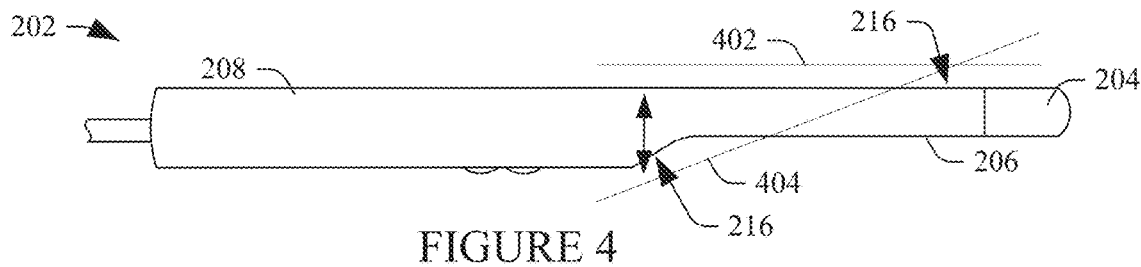
FIG. 4 illustrates a side view of the probe of FIGS. 2 and 3, including a region that limits a range of possible biopsy needle trajectories.

This allows the biopsy trajectory paths to be positioned around one needle perforation site and the entire prostate can be biopsied. An example is shown in FIG. 18, which shows a side view and several needle trajectories 1802, 1804, 1806 and 1808 between a parallel trajectory 1810 above the probe 504 and an angled trajectory 1812 from below the probe 504. This probe configuration mitigates the physical interference (FIGS. 2-4) of the side 1622 of the handle 1606 of the probe 504, which interferes with such needle trajectories. FIG. 18 also shows an image plane 1818 extending from the center line 1618 of the shaft 1610 in the direction only out from the top side 1604 and the sagittal image plane 1818.

Figure 25:
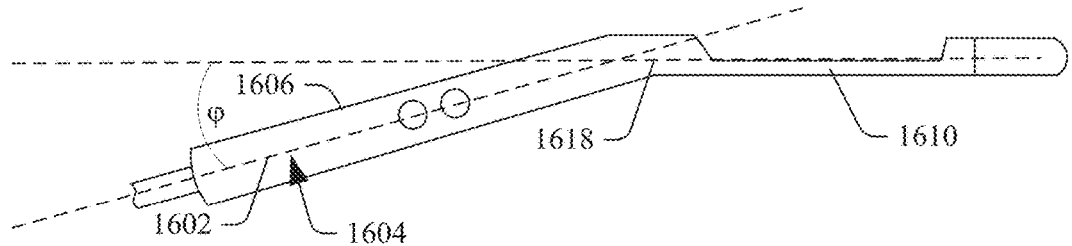
FIG. 25 illustrates a top down view of another example probe configured with its handle angled with respect to the shaft such that it does not interfere with biopsy needle trajectories in accordance with an embodiment(s) herein.

FIG. 25 shows a variation of the probe 504 of FIGS. 16-18 from the top-down view of the probe 504. In this variation, the handle 1606 is instead angled in a plane extending through the handle 1606 and the shaft 1610 that is transverse to the sagittal image plane 1818 of FIG. 18 and sideways with respect to the shaft 1610 by an angle cp. Similar to FIGS. 16 and 17, this allows the trajectories 1802, 1804, 1806 and 1808 shown in FIG. 18 between the parallel trajectory 1810 above the probe 504 and the angled trajectory 1812 from below the probe 504. In another variation, the handle 1606 can be angled as shown in FIG. 25 and the shaft 1610 can be offset as shown in FIG. 16 or FIG. 17.

Figure 26:
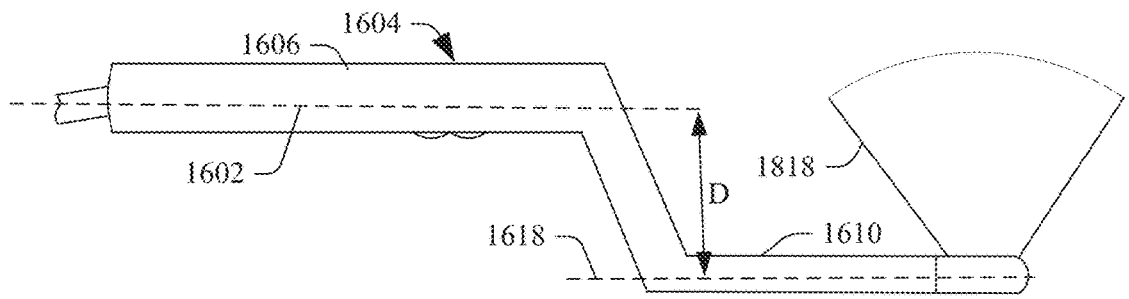
FIG. 26 illustrates a side view of another example probe configured with its handle shifted up in the sagittal plane such that it does not interfere with biopsy needle trajectories in accordance with an embodiment(s) herein.
Figure 20:
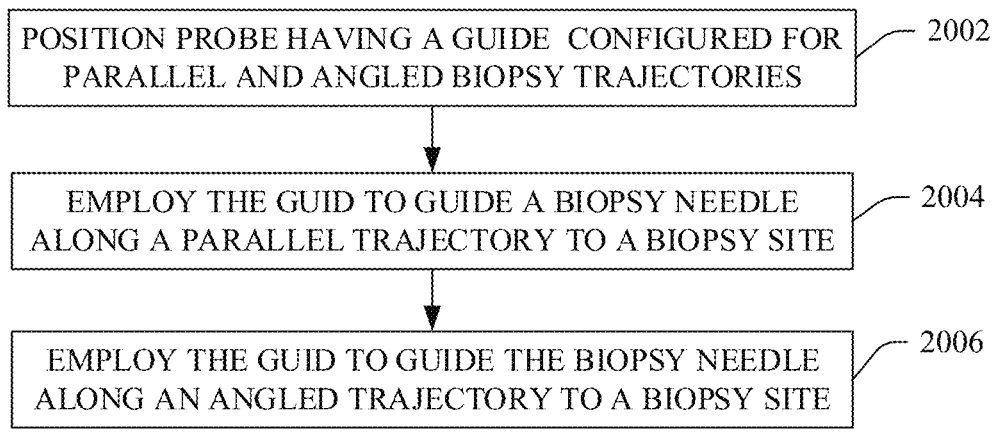
FIG. 20 illustrates an example method in accordance with an embodiment(s) herein.

FIG. 26 shows another variation of the probe 504 of FIGS. 16-18 from the side view. In this variation, the handle 1606 is instead shifted up in the sagittal plane in a direction of the image plane 1818 by a distance "d". Similar to FIGS. 16 and 17, this allows the trajectories 1802, 1804, 1806 and 1808 shown in FIG. 18 between the parallel trajectory 1810 above the probe 504 and the angled trajectory 1812 from below the probe 504. In another variation, the handle 1606 can be shifted as shown in FIG. 20 and angled as shown in FIG. 26 and/or the shaft 1610 can be offset as shown in FIG. 16 or FIG. 17.

In general, with the configurations of FIGS. 16-18, 25 and 26, the elongate tubular handle 1606 is not both centered on the elongate tubular shaft 1610 (like in FIGS. 2-4) and shifted down in the sagittal image plane 1818 away from the top side 1604 of the elongate tubular shaft 1610. In addition, the guide 602 of FIGS. 5-15, 23 and 24 can be employed with the probe of FIGS. 16-18, 25 and 26.

Figure 19:
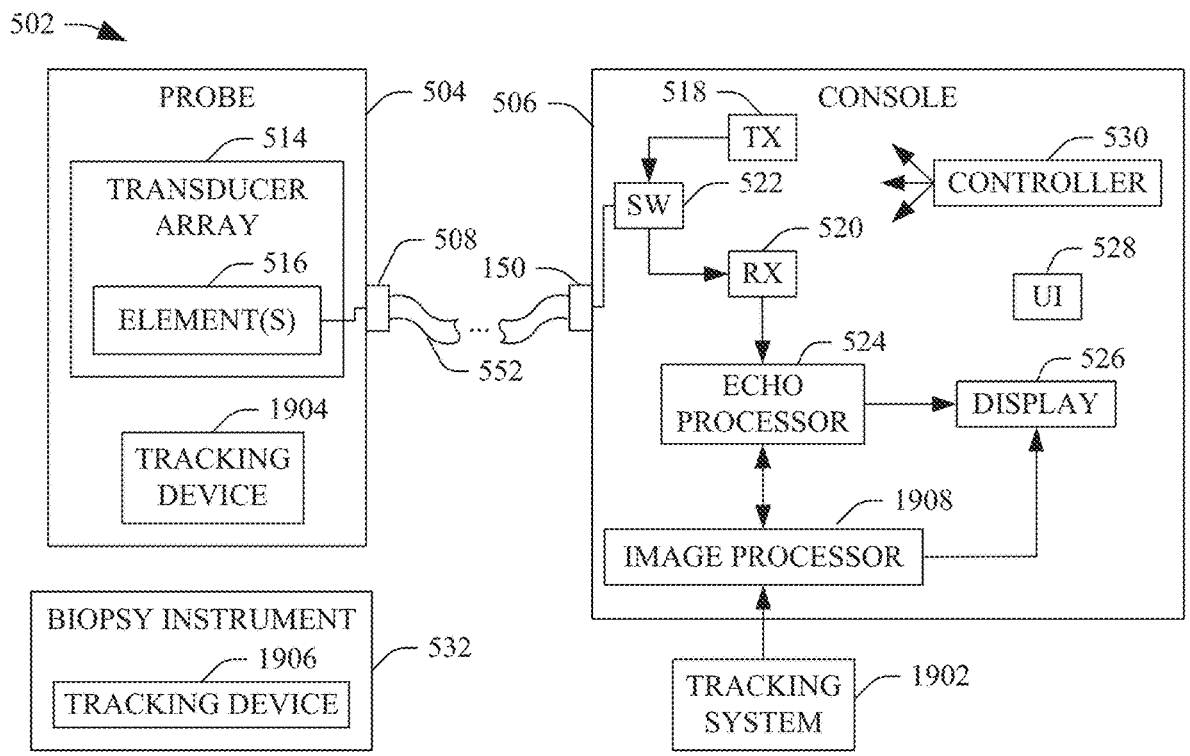
FIG. 19 diagrammatically illustrates the imaging system and the biopsy instrument of FIG. 5 in connection with a needle and transducer array tracking system in accordance with an embodiment(s) herein.

FIG. 19 illustrates a variation of the imaging system 502. In this variation, the probe 504 is configured to acquire three-dimensional volumetric data, the system 502 includes a probe and biopsy instrument tracking system 1902, the probe 504 further includes an internal and/or external tracking device(s) 1904, and the biopsy instrument 532 includes an internal and/or external tracking device(s) 1906. The probe and biopsy instrument tracking system 1902 tracks a spatial location of the biopsy instrument 532 relative to the probe 504 and produces a tracking signal/tracking data indicative thereof. The probe 504 is used to perform a free-hand or guided prostate biopsy.

The console 506 further includes an image processor 1908. The image processor 1908 utilize the tracking signal/tracking data to register spatial coordinate systems of the probe 504 and the biopsy instrument 532 and identify a cross-sectional plane in the 3-D ultrasound data that shows a needle of the biopsy instrument 532 and its trajectory, and this image is displayed via the display 526. Where a pre-procedure scan (e.g., MM, CT, etc.) is available and a target is located in the resulting 3-D data, the image processor 1908 superimposes and registers the pre-procedure 3-D data and the 3-D ultrasound data and selects and displays a plane that shows the needle, its trajectory and the target. This variation provides flexibility of freehand biopsies along with a visual guide and accurate tracking.

Suitable tracking includes electromagnetic, optical, mechanical, etc. With electromagnetic tracking, in one instance, tracking coils are included with both the transducer 514 and a needle of the biopsy instrument 532. The tracking system 1902 measures a magnetic field strength of the coils, which depends on a distance and direction of the coils to the tracking system 1902, and the strength and direction is used to determine location and orientation.

With optical tracking, in one instance, fiducial targets are placed on both the transducer 514 and a needle of the biopsy instrument 532. The tracking system 1902 includes an optical device such as a video camera that records the spatial orientation of the optical elements to determine location and orientation.

With mechanical tracking, in one instance, a passive μ-robot arm (e.g., with 5-6 degrees of freedom) is mounted on the probe 504. The robot arm holds a needle guide that can be turned freely, e.g., in two angles (such as elevation and azimuth), and a tip of the guide can be placed freely at any position within the reach of the arm. Encoders or the like disposed at joints of the robot arm provide position signal, which the tracking system 1902 utilizes to determine the spatial relationship between the transducer array 514 if the probe 504 and the needle the biopsy instrument 532.

Suitable tracking devices and systems are discussed in Birkfellner et al., "Tracking Devices," In: Peters T., Cleary K. (eds) Image-Guided Interventions. Springer, Boston, MA, 2008. Suitable tracking systems are described in U.S. patent application US 2010/0298712 A1, filed Feb. 10, 2010, and entitled "Ultrasound Systems Incorporating Position Sensors and Associated Method," and U.S. Pat. No. 8,556, 815 B2, filed May 6, 2010, and entitled "Freehand Ultrasound Imaging Systems and Methods for Guiding Elongate Instruments," both of which are incorporated herein by reference in their entireties. Another example is discussed in U.S. Pat. No. 7,835,785 B2, filed Oct. 4, 2005, and entitled "DC Magnetic-Based Position and Orientation Monitoring system for Tracking Medical Instruments." Other approaches are also contemplated herein.

With FIGS. 6-19 and 23-26, a biopsy needle can be inserted directly through the perineum and/or through a hollow access channel of an access device (e.g., a trocar) that is inserted directly through the perineum.

FIG. 20 illustrates an example method in accordance with an embodiment herein.

It is to be appreciated that the order of the below acts is not limiting, and in other embodiments, there may be more, less and/or different acts.

At 2002, an ultrasound imaging probe with a guide, which is configured for both parallel and angled biopsy needle trajectories, attached thereto is positioned for a perineal biopsy.

At 2004, the guide guides a biopsy needle along a parallel trajectory to a biopsy site (e.g., the peripheral region of the prostrate) where a sample is acquired.

At 2006, the guide guides the biopsy needle along an angled trajectory to another biopsy site (e.g., the apex of the anterior region of the prostrate) where a sample is acquired.

Optionally, the guide is used to guide the biopsy needle along one or more other parallel and/or angled trajectories to other biopsy site where samples are acquired.

Figure 21:
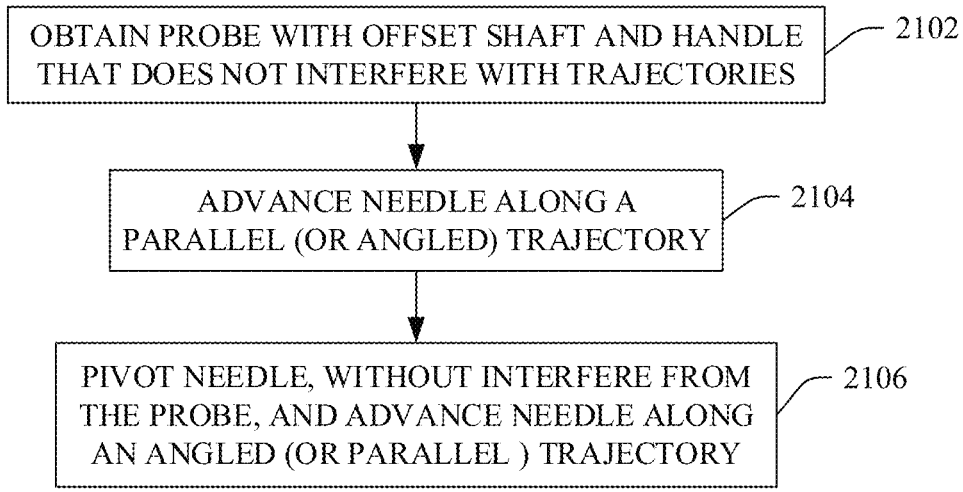
FIG. 21 illustrates another example method in accordance with an embodiment(s) herein.

FIG. 21 illustrates an example method in accordance with an embodiment herein.

It is to be appreciated that the order of the below acts is not limiting, and in other embodiments, there may be more, less and/or different acts.

At 2102, an ultrasound imaging probe with a shaft offset relative of a handle of the probe so as not to physically interfere with biopsy trajectories in a sagittal plane is obtained.

At 2104, a biopsy needle is advanced along the probe via a parallel (or angled) trajectory to a biopsy site where a sample is acquired.

At 2106, the biopsy needle is pivoted, without physical interference of the probe with the trajectory, and advanced along the probe via an angled (parallel) trajectory to a biopsy site where a sample is acquired.

Figure 22:
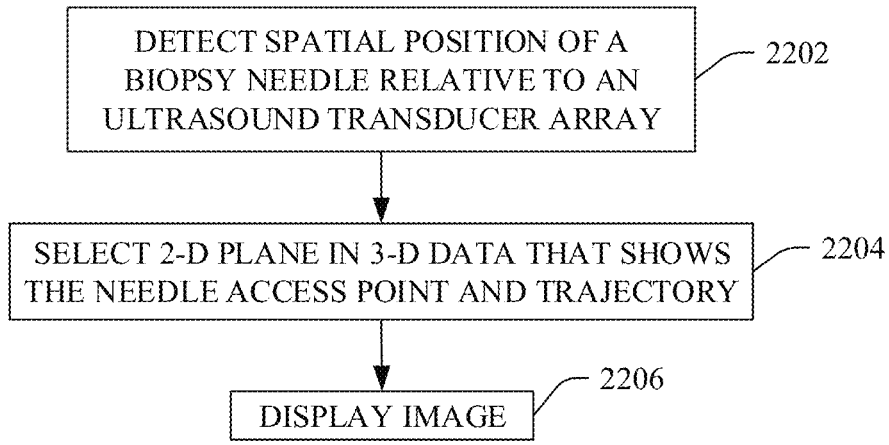
FIG. 22 illustrates yet another example method in accordance with an embodiment(s) herein.

FIG. 22 illustrates an example method in accordance with an embodiment herein.

It is to be appreciated that the order of the below acts is not limiting, and in other embodiments, there may be more, less and/or different acts.

At 2202, a tracking system detects a spatial position of a biopsy needle relative to an ultrasound probe and generates a signal indicative thereof.

At 2204, an image processor selects a 2-D plane of 3-D ultrasound image date that includes an access point and a trajectory of the biopsy needle.

At 2206, the selected 2-D plane is displayed.

Optionally, the selected plane also includes a biopsy target.

The application has been described with reference to various embodiments. Modifications and alterations will occur to others upon reading the application. It is intended that the invention be construed as including all such modifications and alterations, including insofar as they come within the scope of the appended claims and the equivalents thereof.

What is claimed is:

1. A system, comprising:
a needle biopsy guide, including:
a first portion configured to couple to an elongate ultrasound imaging probe;
a hollow channel configured to guide a needle or a cannula along a trajectory that is parallel to a long axis of the elongate ultrasound imaging probe and along a trajectory that is angled to the long axis;
a support configured to couple to a probe;
an access channel configured to support the needle or the cannula;
an actuator with a nub on one end; and
a pivot point;
wherein the actuator is pivotably mounted to the support at the pivot point and configured to move between a position in which the needle or the cannula traverses a trajectory parallel to the long axis of the elongate ultrasound imaging probe and a position in which the nub elastically deforms the needle or the cannula to traverse a trajectory angled to the long axis of the elongate ultrasound imaging probe.

2. The system of claim 1, wherein the elongate ultrasound imaging probe further includes:
a top side that extends along the long axis:
an elongate tubular handle;
a head;
an elongate tubular shaft disposed between the elongate tubular handle and the head; and
a transducer array disposed in the head and configured to transmit in a sagittal plane only in a direction extending out from the top side;
wherein the elongate tubular handle is not centered on the elongate tubular shaft and is not shifted down in the sagittal plane away from the top.

3. The system of claim 1, wherein the elongate ultrasound imaging probe further includes:
a first tracking device;
a needle biopsy instrument including a second tracking device;
a tracking system configured to track a spatial location of the needle biopsy instrument and the elongate ultrasound imaging probe based on signals from the first and second tracking devices;
an image processor configured to select a plane from volumetric image data generated with ultrasound echoes detected by a transducer array of the elongate ultrasound imaging probe based on the tracked spatial locations, wherein the plane includes an entry point of the needle biopsy instrument in an object and at least a trajectory of the needle biopsy instrument in the object; and
a display configured to display the selected plane.

4. A system, comprising:
a needle biopsy guide, including:
a first portion configured to couple to an elongate ultrasound imaging probe;
a hollow channel configured to guide a needle or a cannula along a trajectory that is parallel to a long axis of the elongate ultrasound imaging probe and along a trajectory that is angled to the long axis, wherein the hollow channel includes a common second portion and a third portion with different branching portions, wherein one of the branching portions is for the parallel trajectory and another of the branching portions is for the angled trajectory.

5. A system, comprising:
a needle biopsy guide, including:
a first portion configured to couple to an elongate ultrasound imaging probe;
a hollow channel configured to guide a needle or a cannula along a trajectory that is parallel to a long axis of the elongate ultrasound imaging probe and along a trajectory that is angled to the long axis, wherein the needle biopsy guide further comprising:
a first vertical leg, including:
an opening;
a second portion of a first bearing disposed in the opening; and
a third portion of the first bearing configured to move vertically within the second portion of the first bearing, wherein the third portion is configured to support the needle or the cannula;
a second vertical leg, including:
an opening;
a fourth portion of a second bearing disposed in the opening; and
a fifth portion of the second bearing configured to move vertically within the fourth portion of the second bearing, wherein the fifth portion is configured to support the needle or the cannula; and
a limiter,
wherein the limiter is configured to limit travel of the third portion of the first bearing of the first vertical leg, and the third portion of the first bearing of the first vertical leg and the fifth portion of the second bearing of the second vertical leg are configured to travel between a position providing the parallel trajectory and a position providing the angled trajectory.

6. A system, comprising:
a needle biopsy guide, including:
a first portion configured to couple to an elongate ultrasound imaging probe;
a hollow channel configured to guide a needle or a cannula along a trajectory that is parallel to a long axis of the elongate ultrasound imaging probe and along a trajectory that is angled to the long axis, wherein the hollow channel includes a plurality of hollow channels, and the needle biopsy guide further comprising:
a block, including:
a single column of the plurality of hollow channels,
wherein a hollow channel of the plurality of hollow channels provides a second portion configured to guide the needle or the cannula along the trajectory that is parallel to the long axis and a third portion configured to guide the needle or the cannula along the trajectory that is angled to the long axis.

7. The system of claim 6, wherein the second portion and the third portion of the block partially overlap.

8. The system of claim 6,
wherein the single column of the plurality of hollow channels includes:
a single entry point at a first end of the second portion;
a single path extending through the second portion from the first end to a second opposing end of the second portion;
a first branch segment extending through the third portion from the second opposing end of the second portion and along a first branch path; and a second branch segment extending through the third portion from the second opposing end of the second portion and along a second branch path.

9. The system of claim 8, wherein the single path and the first branch segment provide parallel biopsy needle trajectories, and the single path and the second branch segment provide angled biopsy needle trajectories.

10. A system, comprising:
a needle biopsy guide, including:
  a first portion configured to couple to an elongate ultrasound imaging probe;
  a hollow channel configured to guide a needle or a cannula along a trajectory that is parallel to a long axis of the elongate ultrasound imaging probe and along a trajectory that is angled to the long axis, wherein the hollow channel includes an access channel, and the needle biopsy guide further comprising:
  a support;
  the access channel, wherein the access channel is configured to support the needle or the cannula; and
  an actuator pivotably mounted to the support at a pivot point,
  wherein the access channel is configured to provide a parallel trajectory in response to the actuator being in a non-actuating state, and
  wherein the access channel is configured to provide an angled trajectory in response to the actuator being in an actuating state.

11. The system of claim 10, the actuator including:
a shaft, including:
  a first end; and
  a second end; and
a nub disposed proximal to the second end.

12. The system of claim 11, wherein in the non-actuating state the nub is configured to reside below the access channel and the access channel provides a parallel trajectory.

13. The system of claim 12, wherein in the actuating state the nub physically contacts a portion of the access channel and urges the portion away from the support, which bends or deforms the access channel, providing an angled trajectory.

14. The system of claim 12, wherein in the actuating state the actuator is configured to pivot about the pivot point pivoting the first end in a direction towards the support and pivoting the second end in a direction away from support.

* * * * *